United States Patent [19]

Odenwälder et al.

[11] Patent Number: 5,407,789
[45] Date of Patent: Apr. 18, 1995

[54] PHOTOGRAPHIC RECORDING MATERIAL

[75] Inventors: Heinrich Odenwälder, Leverkusen; Hans Öhlschläger, Bergisch Gladbach; Thomas Stetzer, Langenfeld, all of Germany

[73] Assignee: Agfa-Gevaert AG, Leverkusen, Germany

[21] Appl. No.: 190,686

[22] Filed: Feb. 1, 1994

Related U.S. Application Data

[63] Continuation of Ser. No. 997,221, Dec. 28, 1992, abandoned.

[30] Foreign Application Priority Data

Jan. 9, 1992 [DE] Germany .................. 42 00 322.9

[51] Int. Cl.$^6$ ................................ G03C 1/46
[52] U.S. Cl. .................... 430/504; 430/379; 430/551; 430/603; 430/607; 430/611; 430/613
[58] Field of Search ............ 430/504, 551, 379, 362, 430/382, 603, 607, 611, 613

[56] References Cited

U.S. PATENT DOCUMENTS

| | | | |
|---|---|---|---|
| 3,362,826 | 1/1968 | Weyde et al. | 96/85 |
| 3,536,487 | 10/1970 | Graham | 96/22 |
| 3,761,278 | 9/1973 | Gauss | 430/614 |
| 4,310,621 | 1/1982 | Odenwalder et al. | 430/443 |
| 4,784,938 | 11/1988 | Obhayashi et al. | 430/551 |
| 4,963,466 | 10/1990 | Kajiwara et al. | 430/551 |

FOREIGN PATENT DOCUMENTS

| | | |
|---|---|---|
| 0294149 | 10/1989 | European Pat. Off. . |
| 0462579 | 12/1991 | European Pat. Off. . |
| 2042533 | 3/1972 | Germany . |

*Primary Examiner*—Charles L. Bowers, Jr.
*Assistant Examiner*—Geraldine Letscher
*Attorney, Agent, or Firm*—Connolly & Hutz

[57] ABSTRACT

A photographic recording material on a transparent support having at least one light-sensitive silver halide emulsion layer and optionally conventional interlayers and protective layers, characterized in that the photographic recording material contains, in at least one of the above-mentioned layers, a compound corresponding to formula I, II or III

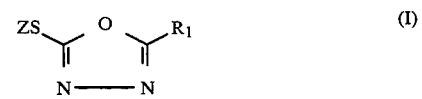

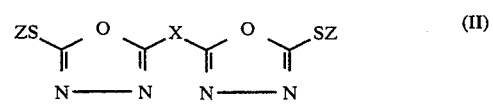

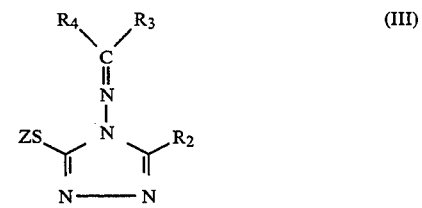

wherein
$R_1$ denotes an unsubstituted or substituted alkyl group, an unsubstituted or substituted aryl group or an unsubstituted or substituted heterocyclic group,
$R_2$ denotes hydrogen, an unsubstituted or substituted alkyl group, an unsubstituted or substituted aryl group or an unsubstituted or substituted alkylthio group,
$R_3$ denotes hydrogen or an unsubstituted or substituted alkyl group,
$R_4$ denotes an unsubstituted or substituted alkyl group, an unsubstituted or a substituted aryl group or an unsubstituted or substituted heterocyclic group,
X denotes an alkylene group having 1 to 8 carbon atoms in which the carbon chain may be interrupted by oxygen or sulphur atoms, or it denotes an arylene group, and
Z denotes hydrogen, a cation or a precursor compound thereof which is capable of releasing the mercapto compound non-imagewise in the course of development, is distinguished by excellent interimage and edge effects and by improved sharpness and graininess compared with conventional materials.

5 Claims, No Drawings

PHOTOGRAPHIC RECORDING MATERIAL

This application is a continuation of application Ser. No. 07/997,221 filed Dec. 28, 1992, now abandoned.

This invention relates to a photographic recording material on a transparent support which is distinguished by high interimage effects and improved sharpness and graininess.

It is known that all modern colour photographic recording materials operate on the principle of subtractive colour production. The general principle of this photographic colour recording consists in producing yellow, magenta and cyan dyes in the positive image so that their concentrations are in inverse ratio to the intensity of the incident blue, green and red light.

Dye formation is based on the formation of developer oxidation products in the exposed areas during development due to the reduction of silver halide to silver, which developer oxidation products react with colourless components in the layers, the so-called colour couplers, to form image dyes. Depending on the nature of these colour couplers, yellow image dyes are obtained from $\beta$-ketoanilides, magenta dyes from pyrazolones and cyan image dyes from $\alpha$-naphthols or phenols.

The nature of the substitution and introduction of the colour couplers into the photographic layer have a decisive influence on the absorption of the image dyes and hence colour reproduction. In the ideal case, the three image dyes should each absorb only in one third of the spectrum. This cannot be realised in practice. Overlapping of the regions of absorption and side absorptions in other spectral regions leading to falsification of colour are particularly disadvantageous.

To overcome such faults, compounds intended to produce a so-called interimage effect have in the past been added to the photographic recording material (e.g. U.S. Pat. No. 3,536,487).

The interimage effect has been described in some detail inter alia by Hanson et al, in Journal of the Optical Society of America, Volume 42, pages 663 to 669 and by A. Thiels, in Zeitschrift für Wissenschaftliche Photographie, Photophysik und Photochemie, Volume 47, pages 106 to 118 and pages 246 to 255.

It is also known that interimage effects can be obtained by the incorporation of DIR compounds (DIR=development inhibitor releasing) in the layers of a photographic material. The DIR compounds may be compounds which split off an inhibitor group and react with the oxidation product of a colour developer to form a dye (DIR couplers) or compounds which release the inhibitor without at the same time forming a dye. The latter are also referred to as DIR compounds in the strict sense. When development inhibitors are released, these are generally heterocyclic mercapto compounds or derivatives of benzotriazole.

It is also known from DE-A-1 447 569 (=U.S. Pat. No. 3,362,826) to add certain heterocyclic mercapto compounds to the baryta layer of a black-and-white photographic paper. These mononuclear and dinuclear mercapto oxadiazoles are intended to prevent the formation of a yellow fog after processing of the material.

In colour reversal materials, however, DIR compounds are of little value for controlling interimage and edge effects since they only become active in the colour developer and inhibitory effects are very difficult to obtain in the colour development of reversal processing.

So-called IRD compounds (IRD=inhibitor releasing developer), however, e.g. DIR hydroquinones disclosed in DE-A-2 952 280, are effective in the first developer of colour reversal development, a black-and-white developer. High interimage and edge effects can be obtained by their inhibitory effects. To this day, however, it has not been possible to overcome one important disadvantage of these compounds, namely their instability. When a photographic material is stored, especially under hot and moist conditions, the instability brings about a change in the properties of the photographic material, e.g. there may be a loss of sensitivity.

It is an object of the present invention to provide a photographic recording material which contains a compound producing an interimage effect but does not have the disadvantages hitherto associated with such a compound.

The invention therefore relates to a photographic recording material on a transparent support having at least one light-sensitive silver halide emulsion layer and optionally conventional interlayers and protective layers, characterised in that the photographic recording material contains, in at least one of the above-mentioned layers, a compound corresponding to the formula I, II or III

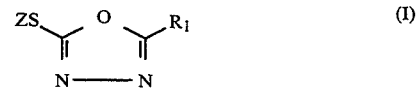

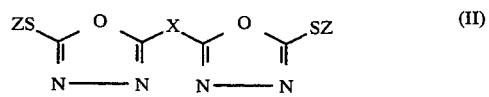

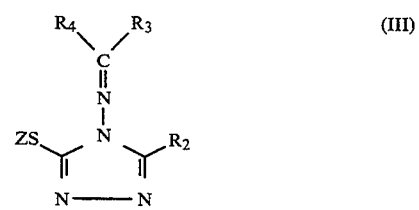

wherein
R1 denotes an unsubstituted or substituted alkyl group, an unsubstituted or substituted aryl group or an unsubstituted or substituted heterocyclic group,
R2 denotes hydrogen, an unsubstituted or substituted alkyl group, an unsubstituted or substituted aryl group or an unsubstituted or substituted alkylthio group,
R3 denotes hydrogen or an unsubstituted or substituted alkyl group,
R4 denotes an unsubstituted or substituted alkyl group, an unsubstituted or substituted aryl group or an unsubstituted or substituted heterocyclic group,
X denotes an alkylene group having 1 to 8 carbon atoms in which the carbon chain may be interrupted by oxygen or sulphur atoms, or it denotes an arylene group, and
Z denotes hydrogen, a cation or a precursor compound thereof which may release the mercapto compound non-imagewise in the course of development.

If one of the groups $R_1$ to $R_4$ is an alkyl group, it is preferably an alkyl group having 1 to 6 carbon atoms.

The alkyl groups may be straight chained, branched or cyclic.

An aryl group is preferably a phenyl group. An aralkyl group is preferably a benzyl group.

Heterocyclic groups are preferably groups derived from furan, thiophene, pyridine or thiazole.

If a substituent is present, it is preferably oxygen, sulphur, nitrogen, fluorine, chlorine or bromine. Particularly preferred groups are, for example, hydroxy, mercapto, alkoxy, alkylthio, alkoxycarbonyl or amino.

When Z is a cation, it is preferably a sodium, magnesium, calcium or ammonium ion. When Z is a precursor compound, it is a group which is split off at pH 8 to 14 in the course of development and replaced by H, e.g. an acetyl, chloroacetyl, methyl sulphonyl ethyl or cyanoethyl group.

Particularly advantageous mercapto oxadiazoles corresponding to Formulae I and II are shown in Table 1.

TABLE 1

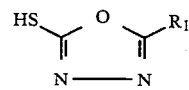

| $R_1$ | Compound |
|---|---|
| —CH₂CH₂— (linked to second oxadiazole ring with SH) | A-1 |
| —(CH₂)₄— (linked to second oxadiazole ring with SH) | A-2 |
| 2-furyl | A-3 |
| 2,3-dichlorophenyl | A-4 |
| 2-hydroxyphenyl | A-5 |
| 4-(NH—COCH₃)phenyl 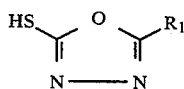 | A-6 |

TABLE 1-continued

| $R_1$ | Compound |
|---|---|
| 4-pyridyl | A-7 |
| 3-(NHCONH—C₄H₉-t)phenyl | A-8 |
| 4-phenyl linked via C(=N)—O—C(SH)=N (oxadiazole) | A-9 |
| 4-(N=CH-2-naphthyl)phenyl | A-10 |
| 4-(N=CH-(2-hydroxyphenyl))phenyl | A-11 |
| 4-(succinimido)phenyl | A-12 |
| —C₆H₁₃ | A-13 |
| —CH₂CH₂—S—CH₂CH₂— (linked to second oxadiazole ring with SH) | A-14 |

Particularly advantageous mercaptotriazoles corresponding to Formula III are shown in Table 2.

TABLE 2

$$\begin{array}{c} R_4 \quad R_3 \\ \diagdown C \diagup \\ \parallel \\ N \\ HS \diagdown \mid \diagup R_2 \\ C \quad N \quad C \\ \parallel \qquad \parallel \\ N \underline{\qquad} N \end{array}$$

| $R_2$ | $R_3$ | $R_4$ | Compound |
|---|---|---|---|
| H | H | phenyl | B-1 |
| H | H | 2-furyl | B-2 |
| H | H | 3,4-methylenedioxyphenyl | B-3 |
| H | H | 2,5-dimethyl-3-furyl | B-4 |
| $C_2H_5$ | H | 4-(OCH(CH$_3$)COOCH$_3$)phenyl | B-5 |
| $CH_3$ | H | 4-hydroxyphenyl | B-6 |
| H | H | 4-methyl-2-(methylthio)thiazol-5-yl | B-7 |
| $-SCH_3$ | H | $-CH(CH_3)_2$ | B-8 |
| $-S-CH_2-COOC_2H_5$ | H | 2-furyl | B-9 |
| phenyl | $CH_3$ | $CH_3$ | B-10 |
| H | H | 4-[CH=N-N(C(SH)=N-N=CH-)]phenyl | B-11 |

Addition of the compounds according to the invention to a colour photographic material provides excellent interimage and edge effects which lead to excellent colour reproduction, reproduction of detail and graininess. In case of a black-and-white photographic material the addition leads to great sharpness and excellent graininess.

Although the compounds according to the invention may be added to any layer of the photographic material, they are preferably added to a light-sensitive silver halide emulsion layer.

The material according to the invention is preferably a colour photographic recording material having at least one red-sensitive, at least one green-sensitive and at least one blue-sensitive silver halide emulsion layer containing, in the given sequence, at least one cyan coupler, at least one magenta coupler and at least one yellow coupler.

In a particularly preferred embodiment, the material according to the invention is a colour reversal material on a transparent support.

The silver halides in the silver halide emulsion layers which contain colour couplers and in those which are free from colour couplers may be AgBr, AgBrI, AgBrCl, AgBrClI or AgCl.

The silver halide emulsions may be negative emulsions or direct positive emulsions.

A photographic recording material in which at least one of the silver halide emulsions used has an iodide content $\geq 4$ mol-% and an average grain diameter $>0.4$ $\mu$m is particularly preferred.

Suitable supports for the production of the material according to the invention are, for example, films of semisynthetic and synthetic polymers, such as cellulose nitrate, cellulose acetate, cellulose butyrate, polystyrene, polyvinyl chloride, polyethylene terephthalate and polycarbonate.

The silver halide may consist predominantly of compact crystals which may e.g. be regular cubes or octahedrons or transitional forms but the silver halide may also contain twinned crystals, e.g. platelet-shaped crystals having an average ratio of diameter to thickness of preferably at least 5:1, the diameter of a grain being defined as the diameter of a circle having the same surface area as the projected surface of the grain. The layers may also contain tabular silver halide crystals in which the ratio of diameter to thickness is greater than 5:1, e.g. from 12:1 to 30:1.

The silver halide grains may also have a multilayered grain structure, in the simplest case with an inner and an outer grain region (core/shell) which may differ from one another in the halide composition and/or other modifications, e.g. doping of the individual grain regions. The average grain size of the emulsions is preferably from 0.2 $\mu$m to 2.0 $\mu$m and the grain size distribution may be either homodisperse or heterodisperse. The emulsions may contain organic silver salts in addition to the silver halide, e.g. silver benzotriazolate or silver behenate.

Two or more types of silver halide emulsions which have been prepared separately may be used as a mixture.

The photographic emulsions may be prepared from soluble silver salts and soluble halides by various methods (e.g. P. Glafkides, Chimie et Physique Photographique, Paul Montel, Paris (1967), G. F. Duffin, Photographic Emulsion Chemistry, The Focal Press, London (1966), V. L. Zelikman et al, Making and Coating Photographic Emulsion, The Focal Press, London (1966).

Precipitation of the silver halide is preferably carried out in the presence of a binder, e.g. gelatine, and may be carried out at an acid, neutral or alkaline pH, preferably with the addition of silver halide complex formers. Examples of the latter include ammonia, thioethers, imidazole, ammonium thiocyanate and excess halide.

The water-soluble silver salts and the halides may be brought together either successively by the single jet process or simultaneously by the double jet process or by any combination of the two processes. They are preferably introduced at increasing flow rates but the "critical" inflow rate at which new nuclei just fail to be formed should not be exceeded. The pAg range may vary within wide limits during precipitation; the so-called pAg controlled process is preferably employed, in which the pAg value is kept constant at a particular level or passed through a definite profile during precipitation. So-called inverse precipitation with silver ion excess may be carried out instead of the preferred method of precipitation with an excess of halide. The silver halide crystals may be made to grow not only by precipitation but also by physical ripening (Ostwald ripening) in the presence of excess halide and/or silver halide complex forming agents. Growth of the emulsion grains may even take place predominantly by Ostwald ripening, in which case a fine-grained, so-called Lippmann emulsion is preferably mixed with a sparingly soluble emulsion and redissolved on the latter.

Salts or complexes of metals such as Cd, Zn, Pb, Tl, Bi, Ir, Rh or Fe may be present during precipitation and/or physical ripening of the silver halide grains.

Precipitation may also be carried out in the presence of sensitizing dyes. Complex forming agents and/or dyes may be rendered ineffective at any stage, e.g. by altering the pH or by an oxidative treatment.

The binder used is preferably gelatine but this may be partly or completely replaced by other synthetic, semisynthetic or naturally occurring polymers. Examples of synthetic gelatine substitutes include polyvinyl alcohol, poly-N-vinyl pyrrolidone, polyacrylamides and polyacrylic acid and derivatives thereof, in particular their copolymers. Examples of naturally occurring gelatine substitutes include other proteins, such as albumin or casein, cellulose, sugar, starch and alginates. Semisynthetic gelatine substitutes are generally modified natural products. Cellulose derivatives such as hydroxyalkyl cellulose, carboxymethyl cellulose and phthalyl cellulose and gelatine derivatives obtained by a reaction with alkylating or acylating agents or by the grafting of polymerisable monomers are examples of these.

The binders should have a sufficient quantity of functional groups so that a reaction with suitable hardeners gives rise to sufficiently resistant layers. Such functional groups are in particular amino groups but also carboxyl groups, hydroxyl groups and active methylene groups.

The gelatine, which is preferably used, may be obtained by acid or alkaline decomposition. The preparation of such gelatines is described, for example, in The Science and Technology of Gelatine, published by A. G. Ward and A. Courts, Academic Press 1977, pages 295 et seq. The gelatine used should be as free as possible from photographically active impurities (inert gelatine). Gelatines with high viscosity and low swelling are particularly advantageous. The gelatine may be partly or completely oxidized.

When crystal formation has been completed or at an earlier stage, the soluble salts are removed from the emulsion, e.g. by shredding and washing, by flocculation and washing, by ultrafiltration or by means of ion exchangers.

The photographic emulsions may contain compounds for preventing fogging or for stabilizing the photographic function during production, storage or photographic processing.

Azaindenes are particularly suitable, especially tetra- and penta-azaindenes and in particular those which are substituted with hydroxyl or amino groups. Such compounds are described e.g. by Birr, Z. Wiss. Phot. 47 (1952), pages 2–58. Salts of metals such as mercury or cadmium, aromatic sulphonic or sulphinic acids such as benzene sulphinic acid and nitrogen-containing heterocyclic compounds such as nitrobenzimidazole, nitroindazole, (substituted) benzotriazoles or benzothiazolium salts may be used as anti-foggants. Heterocyclic compounds containing mercapto groups are particularly suitable, e.g. mercaptobenzothiazoles, mercaptobenzimidazoles, mercaptotetrazoles, mercaptothio-diazoles or mercaptopyrimidines are particularly suitable. These mercaptoazoles may also contain a water-soluble group, e.g. a carboxyl group or a sulpho group. Other suitable compounds are published in Research Disclosure No.17643 (1978), Section VI.

The stabilizers may be added to the silver halide emulsions before, during or after ripening of the emulsions. The compounds may, of course, also be added to other photographic layers associated with a silver halide layer.

Mixtures of two or more of the above-mentioned compounds may also be used.

The silver halide emulsions are normally chemically ripened, for example by the action of gold compounds or compounds of divalent sulphur.

The photographic emulsion layers or other hydrophilic colloid layers of the light-sensitive material prepared according to the invention may contain surface-active agents for various purposes, such as coating auxiliaries, agents to prevent electric charging, to improve the slip properties, to emulsify the dispersion, to prevent adhesion and to improve the photographic characteristics (e.g. development acceleration, high contrast, sensitization, etc.)

Cyanine dyes or suitable sensitizing dyes, in particular those of the following classes:

1. Red sensitizers

Dicarbocyanines containing naphthothiazole or benzothiazole as basic end groups optionally substituted by halogen, methyl or methoxy in the 5- and/or 6-position, and 9,11-alkylene-bridged, in particular 9,11-neopentylene thiadicarbocyanines carrying alkyl or sulphoalkyl substituents on the nitrogen.

2. Green sensitizers

9-Ethyloxacarbocyanines substituted in the 5-position by chlorine or phenyl and carrying alkyl or sulphoalkyl groups, preferably sulphoalkyl substituents, on the nitrogen of the benzoxazole groups.

3. Blue sensitizers

Methine cyanines containing benzoxazole, benzothiazole, benzoselenazole, naphthoxazole or naphthothiazole as basic end groups and optionally substituted by halogen, methyl or methoxy in the 5- and/or 6-position and carrying at least one, preferably two sulphoalkyl substituents on the nitrogen. Also, apomerocyanines containing a rhodanine group.

Sensitizers may be omitted if the intrinsic sensitivity of the silver halide is sufficient for a particular spectral region, for example the blue sensitivity of silver iodobromide ions.

In a colour photographic material, non-diffusible monomers or polymeric colour couplers are associated with the variously sensitized emulsion layers; these compounds may be incorporated in the same layer or in a layer adjacent thereto. Cyan couplers are normally associated with the red-sensitive layers, magenta couplers with the green-sensitive layers and yellow couplers with the blue-sensitive layers.

Colour couplers for producing the cyan partial colour image are generally couplers of the phenol or $\alpha$-naphthol series.

Colour couplers for producing the magenta partial colour image are generally couplers of the 5-pyrazolone series, the indazolone series or the pyrazoloazole series.

Colour couplers for producing the yellow partial colour image are generally couplers having an open chain keto methylene group, in particular couplers of the $\alpha$-acylacetamide series. Examples of these include $\alpha$-benzoyl acetanilide couplers and $\alpha$-pivaloyl acetanilide couplers.

The colour couplers may be 4-equivalent couplers or 2-equivalent couplers. The latter are derived from 4-equivalent couplers in that they carry, in the coupling position, a substituent which is split off in the coupling reaction.

The couplers normally contain a ballast residue to prevent diffusion within the material, i.e. both within a layer and from one layer to another. High molecular weight couplers may be used instead of couplers carrying a ballast residue.

Literature references in which suitable colour couplers are described may be found e.g. in Research Disclosure 17 643 (1978), Chapter VII.

High molecular weight colour couplers are described, for example, in DE-C-1 297 417, DE-A-24 07 569, DE-A-31 48 125, DE-A-32 17 200, DE-A-33 20 079, DE-A-33 24 932, DE-A-33 31 743, DE-A-33 40 376, EP-A-27 284 and U.S. Pat. No. 4,080,211. The high molecular weight colour couplers are generally prepared by the polymerisation of ethylenically unsaturated monomeric colour couplers but they may also be obtained by polyaddition or polycondensation.

The material may also contain compounds capable of releasing a photographically active substance, for example a development inhibitor, a development accelerator, a bleaching accelerator, a developer or a foggant.

Examples of compounds which split off development inhibitors include DIR couplers (see e.g. Research Disclosure 17643 (1978), Chapter VII F) and IRD compounds (see e.g. U.S. Pat No. 4,684,604 and DE-A-31 45 640).

The so-called DAR and FAR couplers are examples of compounds which split off a development accelerator or a foggant (see e.g. DE-A-25 34 466, 34 41 823 and EP-A-0 147 765).

The so-called BAR couplers are examples of compounds which split off a bleaching accelerator (see e.g. EP-A-0 193 389).

Incorporation of the couplers or other compounds in silver halide emulsion layers may be carried out by first preparing a solution, dispersion of emulsion of the particular compound and then adding this to the casting solution for the layer in which it is required. The choice of suitable solvent or dispersing agent depends on the solubility of the compound.

Methods of introducing compounds which are substantially water-insoluble by grinding processes are described, for example, in DE-A-26 09 741 and DE-A-26 09 742.

Hydrophobic compounds may also be introduced into the casting solution by means of high boiling solvents, so-called oil formers. Suitable methods are described, for example, in U.S. Pat. No. 2,322,027, U.S.

Pat. No. 2,801,170, U.S. Pat. No. 2,801,171 and EP-A-0 043 037.

Oligomeric or polymeric compounds, so-called polymeric oil formers, may be used instead of the high boiling solvents.

The compounds may also be introduced into the casting solution in the form of charged latices; see, for example, DE-A-25 41 230, DE-A-25 41 274, DE-A-28 35 856, EP-A-0 014 921, EP-A-0 069 671, EP-A-0 130 115 and U.S. Pat. No. 4,291,113.

The diffusion-fast incorporation of anionic water-soluble compounds (e.g. dyes) may also be carried out with the aid of cationic polymers, so-called mordant polymers.

Examples of suitable oil formers include phthalic acid alkyl esters, phosphonic acid esters, phosphoric acid esters, citric acid esters, benzoic acid esters, amides, fatty acid esters, trimesic acid esters, alcohols, phenols, aniline derivatives and hydrocarbons.

The following are examples of suitable oil formers: Dibutylphthalate, dicyclohexylphthalate, di-2-ethyl hexyl phthalate, decyl phthalate, triphenyl phosphate, tricresyl phosphate, 2-ethyl hexyl diphenylphosphate, tricyclohexyl phosphate, tri-2-ethyl hexyl phosphate, tri-decyl phosphate, tributoxy ethyl phosphate, trichloropropyl phosphate, di-2-ethyl hexyl phenyl phosphate, 2-ethyl hexyl benzoate, dodecyl benzoate, 2-ethyl hexyl-p-hydroxybenzoate, diethyldodecanamide, N-tetradecyl pyrrolidone, isostearyl alcohol, 2,4-di-tert.-amylphenol, dioctyl acetate, glycerol tributyrate, isostearyl lactate, trioctyl citrate, N,N-dibutyl-2-butoxy-5-tert.-octyl aniline, paraffin, dodecylbenzene and diisopropyl naphthalene.

The photographic material may also contain UV light absorbent compounds, white toners, spacers, filter dyes, formalin acceptors, light-protective agents, antioxidants, $D_{min}$ dyes, additives for improving the stabilization of dyes, couplers and whites and for reducing the colour fog, softeners, (latices), biocides, etc.

UV Light absorbent compounds are intended on the one hand to protect the image dyes against bleaching by daylight rich in UV light and on the other hand to act as filter dyes to absorb the UV light of daylight during exposure and thus improve the colour reproduction of a film. Compounds differing in structure are generally used for the two different functions. Examples include aryl substituted benzotriazole compounds (U.S. Pat. No. 3,533,794), 4-thiazolidone compounds (U.S. Pat. Nos. 3,314,794 and 3,352,681), benzophenone compounds (JP-A-2784/71), cinnamic acid ester compounds (U.S. Pat. Nos. 3,705,805 and 3,707,375), butadiene compounds (U.S. Pat. No. 4,045,229) and benzoxazole compounds (U.S. Pat. No. 3,700,455).

Ultraviolet absorbent couplers (such as cyanine couplers of the α-naphthol series) and ultraviolet absorbent polymers may also be used. These ultraviolet absorbents may be fixed in a particular layer by mordanting.

Filter dyes suitable for visible light include oxanol dyes, hemioxonol dyes, styryl dyes, merocyanine dyes, cyanine dyes and azo dyes. Among these dyes, oxonol dyes, hemioxonol dyes and merocyanine dyes are particularly advantageous.

Suitable white toners are described e.g. in Research Disclosure 17643 (December 1978), Chapter V, in U.S. Pat. Nos. 2,632,701 and 3,269,840 and in GB-A-852 075 and 1 319 763.

Certain layers of binders, in particular those furthest removed from the support but occasionally also interlayers, especially if these were furthest removed from the support during preparation of the film, may contain photographically inert particles of an inorganic or organic nature, e.g. of matting agents or as spacers (DE-A-33 31 542, DE-A-34 24 893, Research Disclosure 17643 (December 1978), Chapter XVI).

The average particle diameter of the spacers is in particular in the range of from 0.2 to 10 μm. The spacers are insoluble in water and may be soluble or insoluble in alkalies. Those which are alkali soluble are generally removed from the photographic material in the alkaline development bath. Examples of suitable polymers include polymethyl methacrylate, copolymers of acrylic acid and methyl methacrylate and hydroxypropyl methyl cellulose hexahydrophthalate.

Additives for improving the stability of the dyes, couplers and whites and for reducing the colour fog (Research Disclosure 17643/1978, Chapter VII) may belong to the following classes of chemical substances: Hydroquinones, 6-hydroxychromans, 5-hydroxycoumarans, spirochromans, spiroindans p-alkoxyphenols, sterically hindered phenols, gallic acid derivatives, methylene dioxybenzenes, aminophenols, sterically hindered amines, derivatives containing esterified or etherified phenolic hydroxyl groups, and metal complexes.

Compounds containing both a sterically hindered amine partial structure and a sterically hindered phenol partial structure in 1 molecule (U.S. Pat. No. 4,268,593) are particularly effective in preventing any impairment (deterioration or degradation) of yellow colour images due to the development of heat, moisture or light. Spiroindans (JP-A- 159 644/81) and chromans substituted by hydroquinone diethers or monoethers (JP-A-89 835/80) are particularly effective in preventing impairment (deterioration or degradation) of magenta colour images, in particular impairment (deterioration or degradation) resulting from the action of light.

The layers of the photographic material may be hardened with the usual hardeners. The following are examples of suitable hardeners: Formaldehyde, glutaraldehyde and similar aldehyde compounds, diacetyl, cyclopentadione and similar ketone compounds, bis-(2-chloroethylurea), 2-hydroxy-4,6-dichloro-1,3,5-triazine and other compounds containing reactive halogen (U.S. Pat. No. 3,288,775, U.S. Pat. No. 2,732,303, GB-A-974 723 and GB-A-1 167 207), divinylsulphone compounds, 5-acetyl-1,3-diacryloylhexahydro-1,3,5-triazine and other compounds containing a reactive olefin bond (U.S. Pat. No. 3,635,718, U.S. Pat. No. 3,232,763 and GB-A-994 869); N-hydroxymethyl phthalimide and other N-methylol compounds (U.S. Pat. No. 2,732,316 and U.S. Pat. No. 2,586,168); isocyanates (U.S. Pat. No. 3,101,437); aziridine compounds (U.S. Pat. No. 3,017,280 and U.S. Pat. No. 2,983,611); acid derivatives (U.S. Pat. No. 2,725,294 and U.S. Pat. No. 2,725,295); compounds of the carbodiimide type (U.S. Pat. No. 3,100,704); carbamoyl pyridinium salts (DE-A-22 25 230 and DE-A-24 39 551); carbamoyl oxypyridinium compounds (DE-A-24 08 814); compounds containing a phosphorus-halogen bond (JP-A-113 929/83); N-carbonyloximide compounds (JP-A-43353/81); N-sulphonyloximido compounds (U.S. Pat. No. 4,111,926), dihydroquinoline compounds (U.S. Pat. No. 4,013,468), 2-sulphonyloxypyridinium salts (JP-A-110 762/81), formamidinium salts (EP-A-0 162 308), compounds containing two or more N-acyloximino groups (U.S. Pat. No. 4,052,373), epoxy compounds (U.S. Pat. No.

3,091,537), compounds of the isoxazole type (U.S. Pat. No. 3,321,313 and U.S. Pat. No. 3,543,292); halogen carboxy aldehydes mucochloric acid; dioxane derivatives such as dihydroxydioxane and dichlorodioxane; and inorganic hardeners such as chrome alum and zirconium sulphate.

Hardening may be brought about in known manner by adding the hardener to the casting solution for the layer to be hardened or by covering the layer to be hardened with a layer containing a diffusible hardener.

The classes mentioned above include slow acting hardeners and quick acting hardeners as well as so-called instant hardeners, which are particularly advantageous. Instant hardeners are compound which cross-link suitable binders at such a rate that hardening has been completed to such a stage immediately after casting or at least after 24 hours, preferably after not more than 8 hours, that no further change in sensitometry and swelling of the combination of layers takes place due to the cross-linking reaction. The swelling is the difference between the wet layer thickness and the dry layer thickness of films which are processed under aqueous conditions (Photogr. Sci., Eng. 8 (1964), 275; Photogr. Sci. Eng. (1972), 449).

These hardeners which react very rapidly with gelatine may be, for example, carbamoyl pyridinium salts which are capable of reacting with free carboxyl groups of gelatine so that the latter reacts with free amino groups of gelatine to form peptide bonds and bring about cross-linking of the gelatine.

Some hardeners are diffusible and have an equal hardening action on all layers within a combination of layers while other hardeners, which may be low molecular weight or high molecular weight, are non-diffusible and their action is limited to the layer in which they are contained. These may be used for particularly powerful cross-linking of individual layers, e.g. the protective layer. This is important when the silver halide layer has undergone only little hardening in order to increase the silver covering power and the protective layer is then required for improving the mechanical properties (EP-A 0 114 699).

The black-and-white photographic materials according to the invention are normally processed by development, fixing and washing or stabilizing without subsequent washing. In reversal development, this process is preceded by a first development with subsequent bleaching and a diffuse second exposure or chemical fogging. The developer compounds used for black-and-white development are reducing agents such as phenols, phenolamines and pyrazolinones. Examples of suitable developer compounds include hydroquinone, metol and phenidone.

The colour photographic materials according to the invention are normally processed by development, bleaching, fixing and washing or stabilizing without subsequent washing, and bleaching and fixing may be combined in a single process step. In reversal development, colour development is preceded by a first development with a developer which does not form a dye with the couplers and a diffuse second exposure or chemical fogging.

The developer compounds used for colour development may be any compounds which are capable, in the form of their oxidation product, of reacting with colour couplers to form azomethine or indophenol dyes. Examples of suitable colour developer compounds include aromatic compounds of the p-phenylene diamine series containing at least one primary amino group, for example, N,N-dialkyl-p-phenylenediamine such as N,N-diethyl-p-phenylenediamine, 1-(N-ethyl-N-methanesulphonamidoethyl)-3-methyl-p-phenylenediamine, 1-(N-ethyl-N-hydroxyethyl)-3-methyl-p-phenylenediamine and 1-(N-ethyl-N-methoxyethyl)-3-methyl-p-phenylenediamine. Other suitable colour developers are described, for example, in J. Amer. Chem. Soc. 73, 3106 (1951) and by G. Haist, in Modern Photographic Processing, 1979, John Wiley and Sons, New York, pages 545 et seq.

Colour development may be followed by an acid short stop bath or by washing.

The material is generally bleached and fixed after colour development. The bleaching agents used may be, for example, Fe(III) salts and Fe(III) complex salts such as ferricyanides, dichromates or water-soluble cobalt complexes. Iron-(III) complexes of aminocarboxylic acids are particularly preferred, in particular e.g. the complexes of ethylenediaminotetracetic acid, propylenediaminotetracetic acid, diethylenetriaminopentacetic acid, nitrilotriacetic acid, iminodiacetic acid, N-hydroxyethyl-ethylenediaminotriacetic acid and alkyliminodicarboxylic acids and of corresponding phosphonic acids. Persulphates and peroxides are also suitable bleaching agents, e.g. hydrogen peroxide.

The bleach fixing bath or fixing bath is in most cases followed by washing which is carried out as counter-flow washing or in several tanks each with its own water supply.

Advantageous results may be obtained by following this washing with a final bath containing little or no formaldehyde.

Washing may also be completely replaced by a stabilizing bath, which is normally carried out in counter-flow. This stabilizing bath also takes over the function of a final bath when formaldehyde is added.

EXAMPLE 1

Recording material 1.1

The layers indicated below were applied one after the other to a layer support of cellulose triacetate covered with a substrate layer:

| 1st Layer (Emulsion layer) | |
|---|---|
| Silver halide emulsion | 2.50 g/m² |
| (average grain diameter 0.22 μm, 94 mol-% of bromide, 6 mol-% of iodide) | |
| Silver application in terms of silver nitrate | |
| Coupler C-1 | 2.00 g/m² |
| Gelatine | 5.50 g/m² |
| Tricresylphosphate (TCP) | 1.00 g/m² |
| 2nd Layer (Protective layer) | |
| Gelatine | 1.80 g/m² |
| Hardener H | 1.08 g/m² |

Comparison materials 1.9 to 1.12 and the materials 1.2 to 1.8 according to the invention were obtained in each case by adding 12.5 μmol/m² of the compounds shown in Table 3 to Layer 1. Samples of the materials thus prepared were subjected to colour reversal development after exposure as described in "Manual for PROCESSING Kodak Ektachrome Film using Process E7", Eastman Kodak Company, 1977 (see Kodak Publication No. Z-119).

The edge effect indicated is the difference between the microdensity (width of gap 30 μm) and the macrodensity of reverse developed samples as described in T. H. James, The Theory of the Photographic Process, 4th Edition, Macmillan Publishing Co., Inc., page 611 (1977).

The experimental data thus obtained are shown in Table 3.

TABLE 3

| No. | Compound | Edge effect δD at macrodensity | | | |
|---|---|---|---|---|---|
| | | D = 0.6 | D = 1.0 | D = 1.4 | |
| 1.1 | — | −0.13 | −0.14 | −0.14 | Reference without additive |
| 1.2 | A-1 | −0.49 | −0.75 | −0.89 | |
| 1.3 | A-2 | −0.46 | −0.64 | −0.72 | |
| 1.4 | A-3 | −0.30 | −0.43 | −0.50 | |
| 1.5 | B-1 | −0.41 | −0.56 | −0.62 | |
| 1.6 | B-2 | −0.37 | −0.49 | −0.51 | |
| 1.7 | B-3 | −0.43 | −0.55 | −0.55 | |
| 1.8 | B-4 | −0.38 | −0.49 | −0.50 | |
| 1.9 | V-1 | −0.01 | −0.14 | −0.21 | Comparison |
| 1.10 | V-2 | −0.17 | −0.23 | −0.24 | Comparison |
| 1.11 | V-3 | −0.04 | −0.08 | −0.16 | Comparison |
| 1.12 | V-4 | −0.32 | −0.37 | −0.35 | Comparison |

As may be seen from Table 3, the compounds according to the invention increase the edge effect to a considerable extent whereas the comparison compounds show little or no effect.

EXAMPLE 2

Recording material 2.1

The layers indicated below were applied one after the other to a layer support of cellulose triacetate coated with a substrate layer:

| 1st Layer (red sensitive layer) | |
|---|---|
| Red-sensitized silver halide emulsion (average grain diameter 0.22 μm, 94 mol-% of bromide, 6 mol-% of iodide) Silver application in terms of silver nitrate | 2.50 g/m² |
| Coupler C-1 | 2.00 g/m² |
| Gelatine | 3.00 g/m² |
| TCP | 1.00 g/m² |
| 2nd Layer (interlayer) | |
| Gelatine | 2.15 g/m² |
| Compound S | 0.24 g/m² |
| TCP | 0.12 g/m² |
| 3rd Layer (green sensitive layer) | |
| Green sensitized silver halide emulsion (average grain diameter 0.22 μm, 94 mol-% of bromide, 6 mol-% of iodide) Silver application in terms of silver nitrate | 2.50 g/m² |
| Coupler C-2 | 1.50 g/m² |
| Gelatine | 2.60 g/m² |
| TCP | 0.75 g/m² |
| 4th Layer (protective layer) | |
| Gelatine | 1.80 g/m² |
| Hardener H | 1.08 g/m². |

The test samples 2.2 to 2.10 were obtained in each case by adding 0.5 mmol of the compound shown in Table 4 per 100 g of emulsion (calculated as silver nitrate) to the layers indicated in the Table. Material 2.11 was obtained by replacing the emulsion in the third layer by an emulsion having an average grain diameter of 0.34 μm, 96 mol-% of bromide and 4 mol-% of iodide.

Material 2.12 was obtained by adding 0.5 mmol of the compound indicated in the Table per 100 g of emulsion (calculated as silver nitrate) to Layer 1 of the Material 2.11.

The edge effect was determined as indicated in Example 1. The interimage effect red is the sensitivity difference at D = 1.0 between the red-sensitive layer in a selective exposure red and an additive exposure red+green carried out so that in additive exposure the red sensitivity and green sensitivity were the same. The same applies to the interimage effect green.

TABLE 4

| No. | Compound | Layer | Edge effect δD(at macro-density D = 1.0) | | Interimage effect δE(D = 1.0) | |
|---|---|---|---|---|---|---|
| | | | Cyan | Magenta | Red | Green |
| 2.1 | — | — | −0.10 | −0.15 | 0.2 | 0.2 |
| 2.2 | B-2 | 1 + 3 | −0.58 | −0.63 | 1.6 | 1.4 |
| 2.3 | B-1 | 1 + 3 | −0.72 | −0.79 | 2.2 | 1.2 |
| 2.4 | A-3 | 1 + 3 | −0.39 | −0.43 | 1.4 | 1.0 |
| 2.5 | A-1 | 1 + 3 | −0.83 | −0.84 | 2.0 | 2.0 |
| 2.6 | V-5 | 1 + 3 | −0.49 | −0.48 | 0.6 | 0.5 |
| 2.7 | V-6 | 1 + 3 | −0.20 | −0.57 | 0.0 | 0.4 |
| 2.8 | V-7 | 1 + 3 | −0.41 | −0.50 | 0.6 | 0.8 |
| 2.9 | V-8 | 1 + 3 | −0.20 | −0.20 | 0.2 | 0.2 |
| 2.10 | B-2 | 1 | −0.41 | −0.38 | 2.2 | 0.3 |
| 2.11 | — | — | −0.04 | −0.07 | 0.0 | 0.0 |
| 2.12 | A-3 | 1 | −0.50 | −0.26 | 0.8 | 0.6 |

As may be seen from the Table, the substances according to the invention reinforce the edge effect and interimage effect.

EXAMPLE 3

Recording material 3.1

The layers indicated below were applied one after the other to a layer support of cellulose triacetate coated with a substrate layer:

| 1st Layer (antihalation layer) | |
|---|---|
| Black colloidal silver sol | 0.25 g/m² |
| Gelatine | 1.60 g/m² |
| UV absorbent UV | 0.24 g/m² |
| 2nd Layer (interlayer) | |
| Gelatine | 0.64 g/m² |
| 3rd Layer (first red-sensitive layer) | |
| Red sensitized silver halide emulsion (average grain diameter 0.34 μm, 96 mol-% of bromide, 4 mol-% of iodide) Silver application in terms of silver nitrate | 0.95 g/m² |
| Coupler C-1 | 0.24 g/m² |
| Gelatine | 0.80 g/m² |
| TCP | 0.12 g/m² |
| 4th Layer (second red sensitive layer) | |
| Red-sensitized silver halide emulsion (average grain diameter 0.43 μm, 97 mol-% of bromide, 3 mol-% of iodide) Silver application in terms of silver nitrate | 2.00 g/m² |
| Coupler C-1 | 1.29 g/m² |
| Gelatine | 2.64 g/m² |
| TCP | 0.65 g/m² |
| 5th Layer (interlayer) | |
| Gelatine | 1.78 g/m² |
| Compound S | 0.24 g/m² |
| TCP | 0.12 g/m² |
| 6th Layer (first green-sensitive layer) | |
| Green sensitized silver halide emulsion (average grain diameter 0.34 μm, 96 mol-% bromide, 4 mol-% iodide) Silver application in terms of silver nitrate | 1.05 g/m² |
| Coupler C-3 | 0.22 g/m² |
| Gelatine | 1.0 g/m² |
| TCP | 0.22 g/m² |
| 7th Layer (second green-sensitive layer) | |
| Green sensitized silver halide emulsion (average grain diameter 0.42 μm, 98.5 mol-% of bromide, 1.5 mol-% iodide) Silver application in terms of silver nitrate | 1.65 g/m² |

TABLE 5

| No. | Compound | [μg/m²] layer 3 | [μg/m²] layer 6 | Edge effect δD(at macro-density D = 1.0) Cyan | Edge effect δD(at macro-density D = 1.0) Magenta | Interimage effect δE(D = 1.5) Red | Interimage effect δE(D = 1.5) Green | Interimage effect δE(D = 1.5) Blue | Graininess × 10³ $\sigma_D$(D = 1.0) Cyan | Graininess × 10³ $\sigma_D$(D = 1.0) Magenta | Sharpness [%] 10 line/mm Cyan | Sharpness [%] 10 line/mm Magenta |
|---|---|---|---|---|---|---|---|---|---|---|---|---|
| 3.1 | — | — | — | −0.34 | −0.23 | +0.2 | −0.8 | −1.0 | 34 | 30 | 88 | 96 |
| 3.2 | B-2 | 950 | — | −0.42 | −0.42 | 1.3 | 0.3 | −1.0 | 32 | 30 | 93 | 98 |
| 3.3 | B-2 | — | 530 | −0.45 | −0.48 | 0.6 | 0.5 | −1.0 | 29 | 27 | 89 | 103 |
| 3.4 | B-2 | 950 | 530 | −0.50 | −0.47 | 1.3 | 1.2 | −1.0 | 28 | 25 | 92 | 103 |

As the Table shows, the compound according to the invention improves the edge effect, the interimage effect, the sharpness and the graininess.

| | |
|---|---|
| Coupler C-3 | 1.00 g/m² |
| Gelatine | 2.65 g/m² |
| TCP | 1.00 g/m² |
| 8th Layer (interlayer) | |
| Gelatine | 0.70 g/m² |
| Compound S | 0.10 g/m² |
| TCP | 0.05 g/m² |
| 9th Layer (filter yellow layer) | |
| Yellow colloidal silver sol | 0.19 g/m² |
| Silver application in terms of silver nitrate | |
| Gelatine | 0.75 g/m² |
| 10th Layer (interlayer) | |
| Gelatine | 0.50 g/m² |
| 11th Layer (first blue-sensitive layer) | |
| Blue sensitized silver halide emulsion (average grain diameter 0.52 μm, 95 mol-% bromide, 5 mol-% iodide) | 0.60 g/m² |
| Silver application in terms of silver nitrate | |
| Coupler C-2 | 0.60 g/m² |
| Gelatine | 0.90 g/m² |
| TCP | 0.30 g/m² |
| 12th Layer (second blue-sensitive layer) | |
| Blue sensitized silver halide emulsion (average grain diameter 0.70 μm, 95 mol-% of bromide, 5 mol-% of iodide) | 0.90 g/m² |
| Silver application in terms of silver nitrate | |
| Coupler C-2 | 0.90 g/m² |
| Gelatine | 1.00 g/m² |
| TCP | 0.45 g/m² |
| 13th Layer (interlayer) | |
| Compound S | 0.50 g/m² |
| Gelatine | 2.56 g/m² |
| TCP | 0.02 g/m² |
| UV absorbent UV | 0.55 g/m² |
| 14th Layer (interlayer) | |
| Silver halide emulsion of the Lippmann type (average grain diameter 0.15 μm, 96 mol-% of bromide, 4 mol-% of iodide) | 0.33 g/m² |
| Silver application in terms of silver nitrate | |
| Gelatine | 0.60 g/m² |
| 15th Layer (protective layer) | |
| Hardener H | 1.20 g/m² |
| Gelatine | 0.80 g/m² |

Samples 3.2 to 3.4 were obtained by adding Compound B-2 as shown in Table 5.

The edge effect was determined as described in Example 1. The interimage effect red is the sensitivity difference at D=1.5 between the red-sensitive layer in a selective exposure red and a white exposure (obtained by additive exposure red+green+blue). The same applies to the interimage effects green and blue.

The graininess is the standard deviation $\sigma_D$ of a micro-densitometer trace determined at macrodensity 1.0 as described in T. H. James, The Theory of the Photographic Process, 4th Edition, Macmillan Publishing Co., Inc., page 618 (1977) (Conditions of measurement: Parallel light, measuring diaphragm 28.9 μm). The sharpness (MTF) was determined as described in T. H. James, The Theory of the Photographic Process, 4th Edition, Macmillan Publishing Co., Inc., page 604 (1977).

The components used correspond to the following formulae:

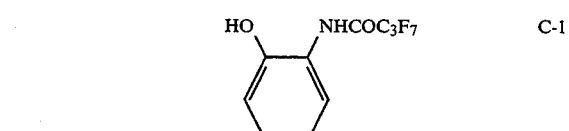

C-1

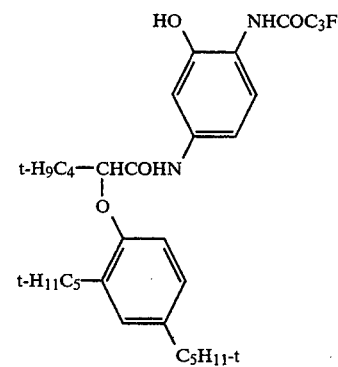

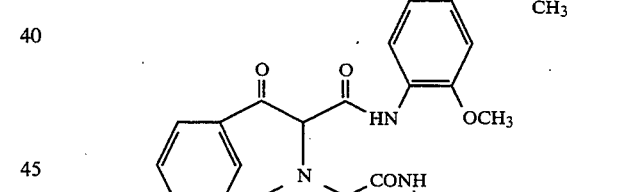

C-2

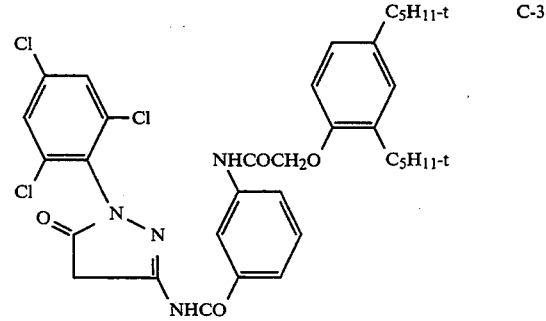

C-3

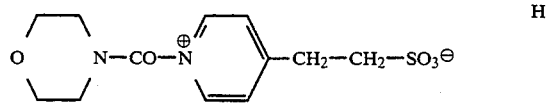

H

-continued

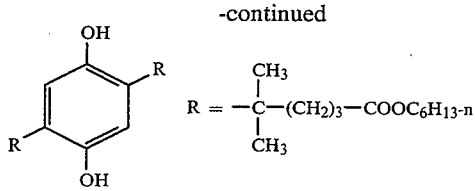

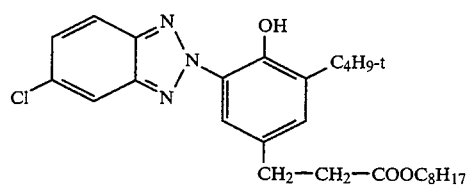

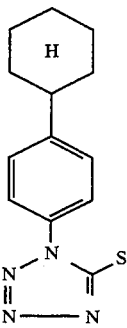

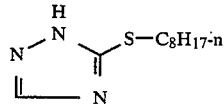

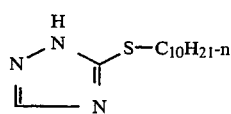

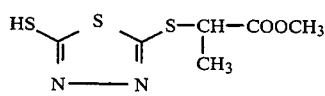

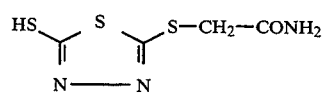

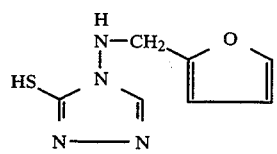

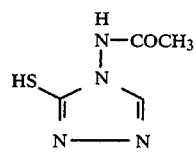

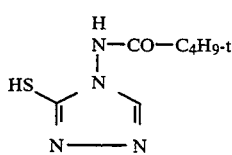

We claim:
1. A photographic recording color reversal material comprising a transparent support having thereon at least one light-sensitive silver halide emulsion layer characterized in that the photographic recording color reversal material contains, in at least one light-sensitive silver halide emulsion layer, a compound corresponding to formula III

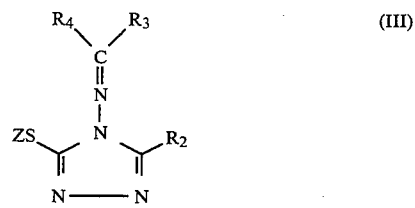

wherein
$R_2$ denotes hydrogen, an alkyl group, an aryl group or an alkylthio group,
$R_3$ denotes hydrogen or an alkyl group,
$R_4$ denotes an alkyl group, an aryl group or an heterocyclic group,
Z denotes hydrogen, a cation or a precursor compound which is capable of releasing the mercapto compound non-imagewise in the course of development.

2. A photographic recording color reversal material according to claim 1, characterized in that at least one of said light-sensitive silver halide emulsion layers contains a silver halide emulsion which has an iodide content of $\geq 4$ mol-% and an average grain diameter of $>0.4$ μm.

3. A photographic recording color reversal material comprising a transparent support having thereon at least one light-sensitive silver halide emulsion layer and non-light-sensitive interlayers and protective layers, characterized in that the photographic recording color reversal material contains, in at least one of the above-mentioned layers, a compound corresponding to formula III

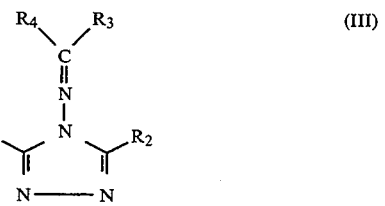

wherein
$R_2$ denotes hydrogen, an alkyl group, an aryl group or an alkylthio group,
$R_3$ denotes hydrogen or an alkyl group,
$R_4$ denotes an alkyl group, an aryl group or a heterocyclic group,
Z denotes hydrogen, a cation or a precursor compound which is capable of releasing the mercapto compound non-imagewise in the course of development.

4. A photographic recording color reversal material according to claim 3, characterized in that the photographic recording material contains a compound corresponding to formula III in a light-sensitive silver halide emulsion layer.

5. A photographic recording color reversal material according to claim 3, characterized in that in at least one of said light-sensitive silver halide emulsion layers contains a silver halide emulsion which has an iodide content of $\geq 4$ mol-% and an average grain diameter of $>0.4$ μm.

* * * * *

UNITED STATES PATENT AND TRADEMARK OFFICE
CERTIFICATE OF CORRECTION

PATENT NO. : 5,407,789
DATED : April 18, 1995
INVENTOR(S) : ODENWALDER ET AL.

It is certified that error appears in the above-indentified patent and that said Letters Patent is hereby corrected as shown below:

On the title page,

In the "References Cited" section, on the cover page of the patent, a subsection entitled, "OTHER PUBLICATIONS" should be inserted with the following article listed thereunder.

Subtractive Color Reproduction: Interimage Effects, W.T. Hanson, Jr. and C.A. Horton, Kodak Research Laboratories, Eastman Kodak Co., Journal of the Optical Society of America, Vol. 42, No. 9, Sept. 1952.

In Claim 2, (Column 20, line 29) " $>0.4$ $\mu$m" should read -- $\leq 0.4$ $\mu$m --; and in Claim 5, (Column 20, line 67)" $>0.4$ $\mu$m" should read -- $\leq 0.4$ $\mu$m --.

Signed and Sealed this

Thirtieth Day of July, 1996

*Attest:*

BRUCE LEHMAN

*Attesting Officer*     *Commissioner of Patents and Trademarks*